United States Patent
Hirooka

(10) Patent No.: US 10,352,913 B2
(45) Date of Patent: Jul. 16, 2019

(54) DATA PROCESSING DEVICE FOR COMPREHENSIVE TWO-DIMENSIONAL CHROMATOGRAPH

(71) Applicant: SHIMADZU CORPORATION, Kyoto-shi, Kyoto (JP)

(72) Inventor: Megumi Hirooka, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 670 days.

(21) Appl. No.: 14/438,259

(22) PCT Filed: Oct. 25, 2012

(86) PCT No.: PCT/JP2012/077540
§ 371 (c)(1),
(2) Date: Jul. 8, 2015

(87) PCT Pub. No.: WO2014/064790
PCT Pub. Date: May 1, 2014

(65) Prior Publication Data
US 2015/0346171 A1  Dec. 3, 2015

(51) Int. Cl.
*G01N 30/46* (2006.01)
*G01N 30/86* (2006.01)
*G01N 30/88* (2006.01)

(52) U.S. Cl.
CPC ....... *G01N 30/8651* (2013.01); *G01N 30/463* (2013.01); *G01N 30/8675* (2013.01); *G01N 2030/8854* (2013.01)

(58) Field of Classification Search
CPC ....... G01N 30/8651; G01N 2030/8854; G01N 30/463; G01N 30/46; G01N 30/8675–30/8689
See application file for complete search history.

(56) References Cited

FOREIGN PATENT DOCUMENTS

JP  2011-122822 A  6/2011

OTHER PUBLICATIONS

Communication dated Dec. 9, 2015, from the State Intellectual Property Office of People's Republic of China in counterpart Application No. 201280076616.6.
(Continued)

*Primary Examiner* — Amar Movva
(74) *Attorney, Agent, or Firm* — Sughrue Mion, PLLC

(57) ABSTRACT

In a GC×GC data processor (23), a modulation time estimation unit (24) creates a one-dimensional chromatogram from chromatogram data items collected by a comprehensive two-dimensional GC, and retrieves a shift time on which a peak position after an entire curve of the chromatogram being shifted in a temporal axis direction coincides with a peak position of the peak on the original chromatogram. Since the resolution of a primary column (12) is low, the same compound is introduced into a secondary column (14) in consecutive modulation times. Accordingly, on the one-dimensional chromatogram, peaks originating from the same compound appear in the respective consecutive modulation times. The interval between the peaks substantially coincides with the modulation time. Therefore, the shift time retrieved as described above is regarded as the modulation time. Thus, the modulation time is automatically estimated from the chromatogram data items, thereby negating the need of user input or capture from an analysis control unit (3).

4 Claims, 3 Drawing Sheets

(56) References Cited

OTHER PUBLICATIONS

Kallio et al; "Semi-rotating cryogenic modulator for comprehensive two-dimensional gas chromatography"; Anal Bioanal Chem, 2003; 375, pp. 725-731, Mar. 11, 2003.
Lu Xin; "Methodology Study on Comprehensive two-dimensional Gas Chromatography/Time of Flight Mass Spectroscopy used for Complex System Analysis"; China Doctoral Thesis Full-text Database, Engineering Science and Technology vol. 1, No. 8: Dec. 15, 2005, 5 pages total.
"GC Image GCxGC Software", [online], [searched on Oct. 17, 2012], GC Image LLC in the U.S.
"GC Image (GCxGC Edition) Users' Guide File Input and Output", [online], [searched on Oct. 17, 2012], GC Image LLC in the U.S.
Written Opinion of the International Searching Authority in PCT/JP2012/077540 dated Jan. 29, 2013.

Fig. 2A ONE-DIMENSIONAL CHROMATOGRAM
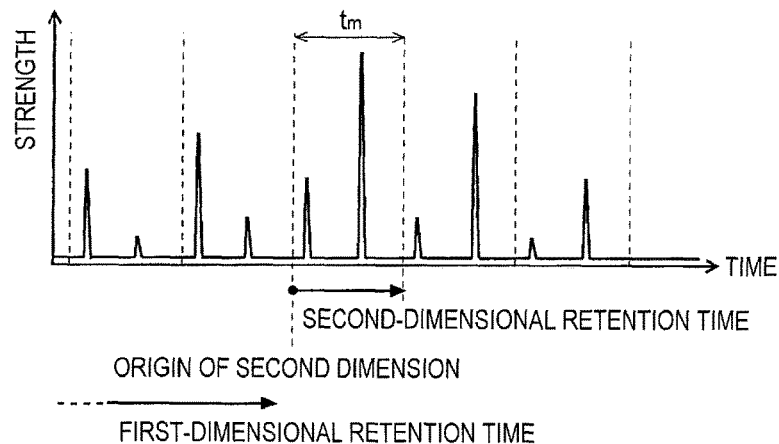
Fig. 2B CREATION ORDER OF TWO-DIMENSIONAL CHROMATOGRAM
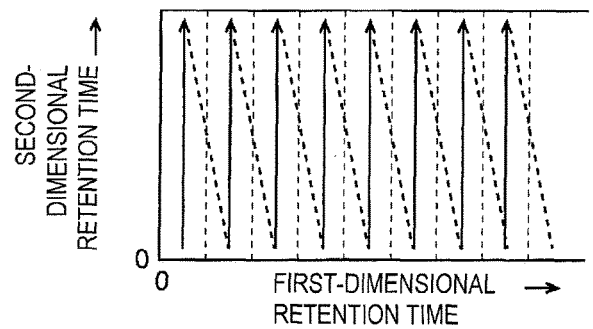
Fig. 2C TWO-DIMENSIONAL CHROMATOGRAM
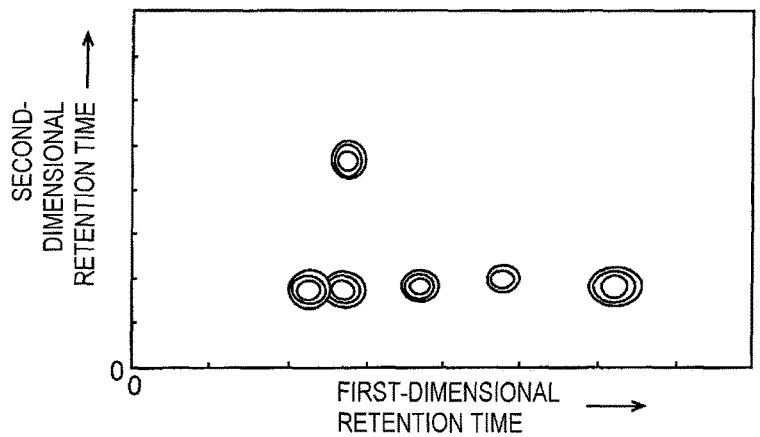

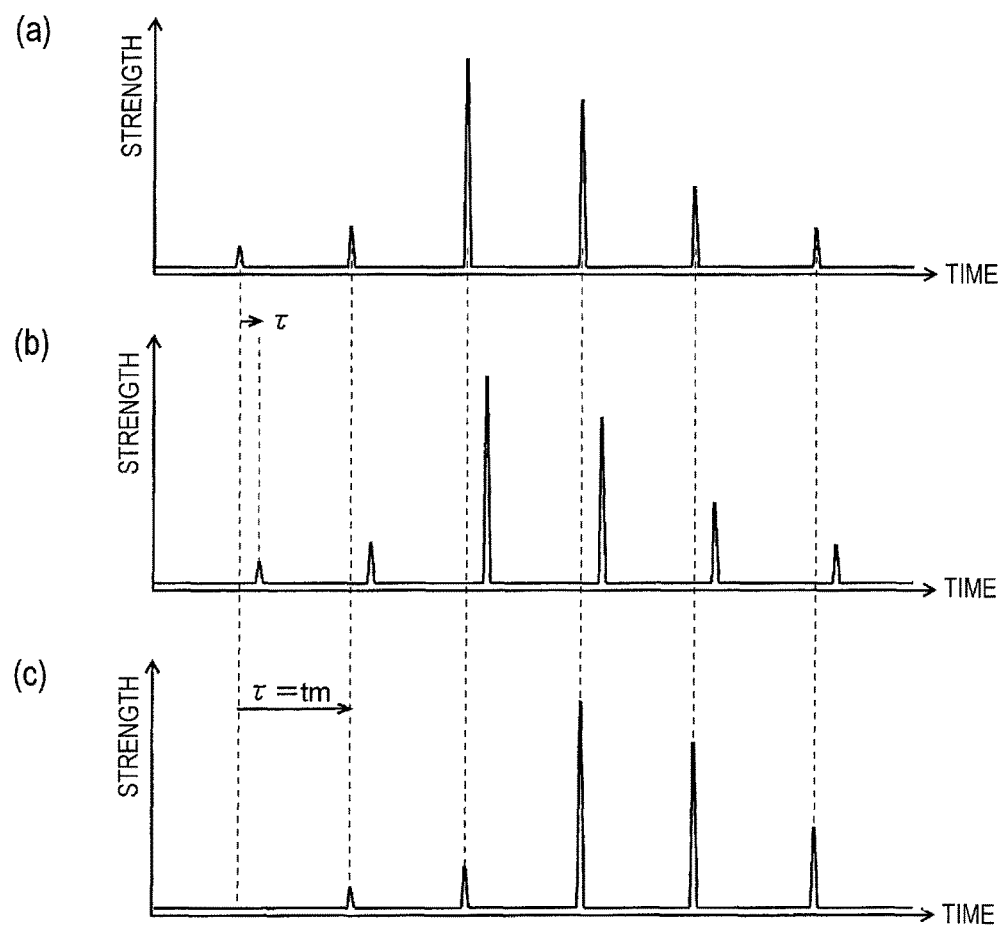

DATA PROCESSING DEVICE FOR COMPREHENSIVE TWO-DIMENSIONAL CHROMATOGRAPH

CROSS REFERENCE TO RELATED APPLICATIONS

This application is a National Stage of International Application No. PCT/JP2012/077540 filed Oct. 25, 2012, the contents of all of which are incorporated herein by reference in their entirety.

TECHNICAL FIELD

The present invention relates to a data processing apparatus for a comprehensive two-dimensional chromatograph, the apparatus processing data collected by a comprehensive two-dimensional gas chromatograph (GC) or a comprehensive two-dimensional liquid chromatograph (LC).

BACKGROUND ART

As a GC analysis technique, a technique called a comprehensive two-dimensional GC (also called "GC×GC") is known (refer to Patent Literature 1). The comprehensive two-dimensional GC first separates various components in a sample in a first-dimension column (hereinafter, called a "primary column"), and introduces the eluted components into a modulator. The modulator repeats an operation of trapping the introduced components at constant time intervals (typically, about several seconds to several tens of seconds; the time interval is usually called "modulation time") and subsequently drawing the components in a significantly narrow time band, and introducing the components into a second-dimension column (hereinafter, called a "secondary column"). Typically, in the primary column, components are separated under a separation condition that allows elution similar to that of a typical GC or elution slightly slower than that of a typical GC. On the other hand, as a secondary column, a column that has a different polarity and a smaller inner diameter in comparison with the primary column is adopted. Components are separated under a condition that allows elution to be completed in a predetermined modulation time.

Accordingly, in the comprehensive two-dimensional GC, the secondary column can be used to separate multiple compounds that have not been separated in the primary column and have peaks overlap with each other, thereby allowing the separation performance to be significantly improved in comparison with a typical GC. Therefore, this GC is significantly effective in analyzing a sample that contains many compounds having close retention times, typically in analyzing hydrocarbons in diesel fuel and the like.

Unlike a multi-dimensional GC that adopts multiple detectors corresponding to respective columns, the comprehensive two-dimensional GC obtains a detection signal through a single detector connected at an output port of a secondary column. Accordingly, though components are separated in columns in two stages, data output from the detector is one series of chronological order data items. Therefore, by plotting the thus obtained data items in the occurrence order, a chromatogram similar to that of a typical GC, i.e., a chromatogram where the abscissa indicates the temporal axis and the ordinate indicates the signal strength axis, can be created. FIG. 2A indicates an example of a one-dimensional chromatogram created in this way.

As described above, in many cases, the comprehensive two-dimensional GC includes two columns having different separation characteristics. Accordingly, in order to represent the state of separation in each column in a manner easy to understand, a two-dimensional chromatogram is created where the retention time in the primary column and the retention time in the secondary column are represented in respective two axes orthogonal to each other and the signal strength is represented as contour lines, or a three-dimensional chromatogram is created where the signal strength is represented as the third axis. As data processing software dedicated to a comprehensive two-dimensional GC for creating such a multi-dimensional chromatogram, "GC Image" (refer to Non Patent Literature 1) provided by GC Image LLC in the U.S. is well known.

FIG. 2B is an explanatory diagram of data arrangement which results when a two-dimensional chromatogram is created from the one-dimensional chromatogram data as shown in FIG. 2A. The range of the ordinate of this graph indicates the modulation time. An operation is repeated that sequentially plots the one-dimensional chromatogram data along the ordinate from the bottom (0) in the upward direction (solid arrows in the diagram), and, upon reaching the modulation time, moves along the abscissa in the right direction while returning to the bottom of the ordinate (broken lines in the diagram), and plots the data again in the upward direction along the ordinate. This repetition can create, for example, a two-dimensional chromatogram (two-dimensional contour line chromatogram) as shown in FIG. 2C.

In a temperature rising analysis, the abscissa indicates the order of boiling points, and the ordinate indicates the polarity order. Accordingly, this two-dimensional chromatogram can facilitate understanding of the characteristics of each compound, and identifying contained compounds even when many types of compounds are contained.

Typically, in the comprehensive two-dimensional GC, data obtained from sample analysis is temporarily stored in a storage device, such as a hard disk. Subsequently, the data is read from the storage device at an appropriate timing, and processed by the dedicated data processing software as described above. The processes of collecting data from the comprehensive two-dimensional GC and storing the collected data in the storage device are performed using software for a typical GC or GC/MS instead of the comprehensive two-dimensional GC. However, the typical GC does not originally have a concept of "modulation time". Accordingly, the collected chromatogram data does not contain data (parameter information) that indicates the modulation time as one of analysis conditions. Thus, conventionally, an analyst records modulation time information during execution of analysis. When the chromatogram data is read by the data processing software dedicated to the comprehensive two-dimensional GC, the analyst inputs the modulation time as one of processing parameters (refer to Non Patent Literature 2). Such operations are complicated for the analyst, and cause a possibility that input errors and the like generate incorrect results.

The comprehensive two-dimensional LC that executes analysis similar to that of the comprehensive two-dimensional GC is also in situations similar to the above situations.

CITATION LIST

Patent Literature

[Patent Literature 1] JP 2011-122822 A

Non Patent Literature

[Non Patent Literature 1] "GC Image GC×GC Software", [online], GC Image LLC in the U.S., [searched on Oct. 17, 2012] GC Image LLC in the U.S., Internet

[Non Patent Literature 2] "GC Image (GC×GC Edition) Users' Guide File Input and Output", [online], GC Image LLC in the U.S., [searched on Oct. 17, 2012], Internet

SUMMARY OF INVENTION

Technical Problem

The present invention has been made in view of the above problems and is addressed to an object to provide a data processing apparatus for a comprehensive two-dimensional chromatograph that can negate the need to input modulation time information required for processing in data processing, such as two-dimensional chromatogram creating, based on chromatogram data obtained through a comprehensive two-dimensional chromatograph.

Solution to Problem

To solve the aforementioned problems, the present invention provides a data processing apparatus for a comprehensive two-dimensional chromatograph, the apparatus processing chromatogram data collected by the comprehensive two-dimensional chromatograph including a primary column, a modulator, a secondary column, and a detector, the data processing apparatus including:

a) a one-dimensional chromatogram creation unit configured to arrange chromatogram data items acquired by the comprehensive two-dimensional chromatograph according to a chronological order to create a one-dimensional chromatogram that represents a relationship between time and signal strength; and b) a modulation time estimation unit configured to estimate modulation time in the modulator, based on regularity in appearance time on the one-dimensional chromatogram between a certain peak and one or more other peaks that originate from a compound identical to the compound for the peak but appear at different time.

Here, the comprehensive two-dimensional chromatograph may be any of a comprehensive two-dimensional GC, and a comprehensive two-dimensional LC.

In general, the peak width of a compound separated in the primary column is large. Accordingly, the same compound is introduced into the secondary column over consecutive ranges of modulation time. Therefore, in the chromatogram data corresponding to the ranges of modulation time, peaks originating from the same compound must regularly appear, and the interval between peaks originating from the same compound on the one-dimensional chromatogram in adjacent two ranges of modulation time must be substantially identical to the modulation time. Thus, in the data processing apparatus for a comprehensive two-dimensional chromatograph according to the present invention, the modulation time estimation unit estimates the modulation time using the regularity of appearance of peaks originating from the same compound on the aforementioned one-dimensional chromatogram.

An aspect of the present invention can have a configuration where the modulation time estimation unit examines correlation between the one-dimensional chromatogram and a time-shifted one-dimensional chromatogram obtained by shifting the one-dimensional chromatogram in a temporal axis, and estimates that a shift time maximizing the correlation during variation in the shift time is the modulation time. More specifically, for example, the product of signal strengths in respective times on between the one-dimensional chromatogram and the time-shifted one-dimensional chromatogram is calculated, and the integrated value over the entire measurement time range is obtained. The variation in integrated value according to variation in shift time may be obtained to find a shift time maximizing the integrated value, and this shift time may be estimated as the modulation time.

Such a configuration can estimate the modulation time through repetition of a simple operation. The repetition has a small load on hardware. Accordingly, the modulation time can be estimated in a short time.

Preferably, the data processing apparatus for a comprehensive two-dimensional chromatograph according to the present invention has a configuration that further includes a two-dimensional chromatogram creation unit configured to create a two-dimensional chromatogram having axes that are retention time in the primary column and retention time in the secondary column, based on the modulation time obtained by the modulation time estimation unit.

Advantageous Effects of Invention

According to the data processing apparatus for a comprehensive two-dimensional chromatograph according to the present invention, based on one-dimensional chromatogram data collected by a comprehensive two-dimensional GC or a comprehensive two-dimensional LC, modulation time is automatically obtained. Accordingly, during execution of data processing specific to a comprehensive two-dimensional chromatograph, such as two-dimensional chromatogram creation through use of modulation time information, the modulation time information is not required to be input from the outside. This negates the need of efforts by the analyst for information input, thereby improving operation efficiencies, and avoiding inappropriate data processing due to an input error or the like.

BRIEF DESCRIPTION OF DRAWINGS

FIG. 2A shows an example of a one-dimensional chromatogram created based on data collected by a comprehensive two-dimensional GC; FIG. 2B is an explanatory diagram of procedures of creating a two-dimensional chromatogram based on one-dimensional chromatogram data; and FIG. 2C is a diagram showing an example of the created two-dimensional chromatogram.

FIG. 3 includes explanatory diagrams (a), (b) and (c) of a modulation time estimating process in the comprehensive two-dimensional GC system of this embodiment.

DESCRIPTION OF EMBODIMENTS

Figure 1:
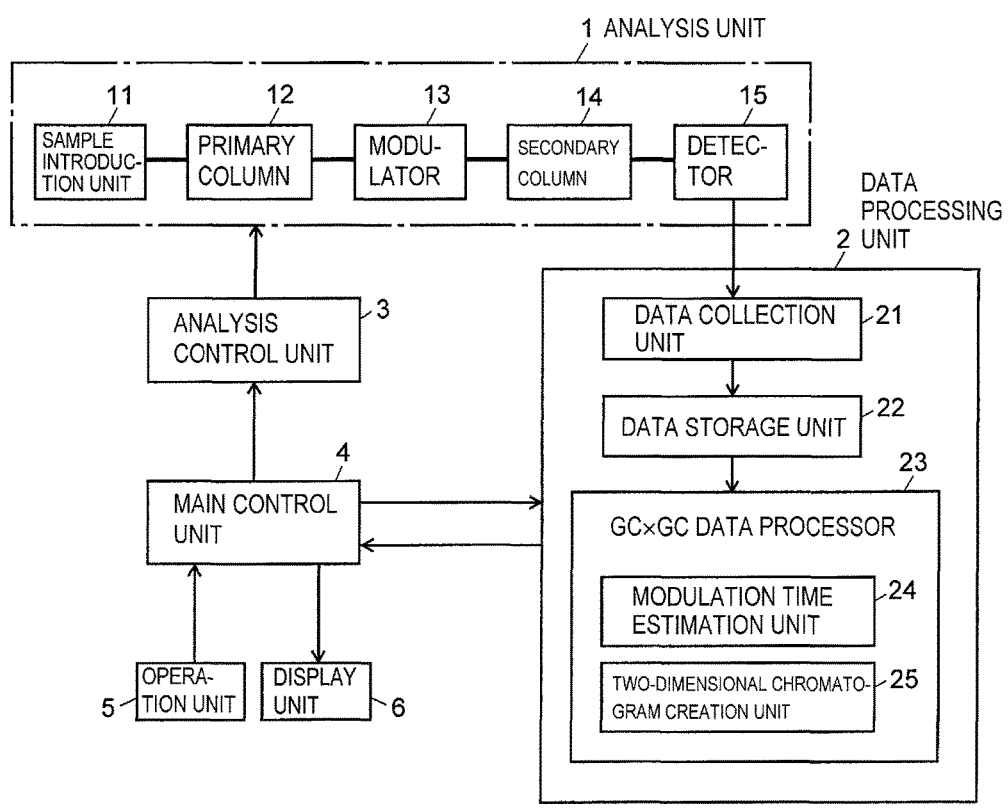
FIG. 1 is a schematic configuration diagram of one embodiment of a comprehensive two-dimensional GC system that includes a data processing apparatus for a comprehensive two-dimensional chromatograph according to the present invention.

One embodiment of a comprehensive two-dimensional GC system adopting a data processing apparatus for a comprehensive two-dimensional chromatograph according to the present invention will be described below with reference to the accompanying drawings. FIG. 1 is a schematic configuration diagram of the comprehensive two-dimensional GC system according to this embodiment.

In this system, an analysis unit 1 includes: a primary column 12; a sample introduction unit 11 that includes a sample vaporization chamber for introducing sample gas into the primary column 12; a modulator 13 that traps components (compounds) eluted from the primary column 12 in constant time (modulation time t) intervals, and temporally compresses and transfers the components; a secondary column 14 that has separation characteristics (typically, different polarity) different from those of the primary column 12 and is capable of high speed separation; and a detector 15 that detects compounds separated in two-stage columns 12 and 14 respectively, and outputs a strength signal according to the detected amount (concentration). The detector 15 may have any configuration that can be generally used as a detector for GC, irrespective of the type (detection scheme). For example, in the case of adopting a mass spectrometer as the detector 15, the mass spectrometer repeatedly performs scanning measurement in a range of predetermined mass-to-charge ratio, and total ion chromatogram data in which the ion intensity data item obtained in each scanning is accumulated be output from the detector 15.

A data processing unit 2 includes: a data collection unit 21 that collects chromatogram data items sequentially output from the detector 15 according to the time lapse as described above; a data storage unit 22 that stores the collected chromatogram data items; and a GC×GC data processor 23 that reads the data items stored in the data storage unit 22, and processes the data items. The GC×GC data processor 23 includes: a modulation time estimation unit 24 that estimates the modulation time $t_m$ based on the read data items; and a two-dimensional chromatogram creation unit 25 that creates a two-dimensional chromatogram based on the estimated modulation time $t_m$.

The operation of each component included in the analysis unit 1 is controlled by an analysis control unit 3. A main control unit 4, to which an operation unit 5 as a user interface and a display unit 6 are connected, performs overall control of the system. The main control unit 4, the analysis control unit 3, and the data processing unit 2 can be achieved by adopting a personal computer as hardware resources, and executing dedicated control/processing software having been preliminarily installed in the personal computer. Particularly, in the GC×GC data processor 23, functions other than the modulation time estimation unit 24 can be achieved using software described in Non Patent Literatures 1 and 2.

An analysis operation in the analysis unit 1, that is, a chromatogram data collecting operation, is schematically described.

In the analysis unit 1, the sample introduction unit 11 introduces a sample to be analyzed into carrier gas transferred to the primary column 12 at a substantially constant flow rate, according to an instruction from the analysis control unit 3. Typically, the sample contains many compounds. The various compounds contained in the sample are separated while passing through the primary column 12 temperature-controlled according to a predetermined temperature rising program, and are eluted by being shifted in time. At this time, not all the compounds are necessarily separated sufficiently. Compounds having close retention times in the primary column 12 are eluted in an overlapping manner (in a mixed state).

The modulator 13 repeatedly performs operations that trap all compounds eluted from the primary column 12 over the modulation time $t_m$ (typically, about several seconds to several tens of seconds), temporally compress the compounds, and transfer the compounds into the secondary column 14 in a significantly narrow band. Accordingly, compounds eluted from the primary column 12 are transferred into the secondary column 14 without exception. The multiple compounds transferred in every modulation time $t_m$ are eluted while being temporally separated at a high resolution during passing through the secondary column 14, and introduced into the detector 15 in the elution order. As described above, in the case of adopting a mass spectrometer as the detector 15, scanning measurement at an interval shorter than a time width in which one compound is eluted from the secondary column 14 allows all the compounds to be detected without exception.

The detection signal by the detector 15 is converted by an internally included A/D converter into digital data at a predetermined sampling period, and output. The data collection unit 21 collects the chromatogram data items sequentially obtained according to the time lapse in this manner, and stores the data items in the data storage unit 22. Typically, a series of chromatogram data items obtained by execution of comprehensive two-dimensional GC analysis for one sample is integrally stored as one data file.

The GC×GC data processor 23 is a dedicated data processing unit for processing data obtained by the comprehensive two-dimensional GC analysis as described above. Typically, the GC×GC data processor has a function of creating a two-dimensional chromatogram where the abscissa indicates a first-dimensional retention time and the ordinate indicates a second-dimensional retention time. In contrast, the GC×GC data processor 23 of this embodiment not only includes the two-dimensional chromatogram creation unit 25, but also the characteristic modulation time estimation unit 24. Hereinafter, description will be made mainly on the operations of the modulation time estimation unit 24. FIG. 3 is explanatory diagrams (a), (b) and (c) of a modulation time estimating process in the modulation time estimation unit 24.

For example, when an operation by the analyst through the operation unit 5 instructs creation of a two-dimensional chromatogram on the basis of the analysis result of the predetermined sample, the GC×GC data processor 23 reads designated data items from the data storage unit 22 based on control by the main control unit 4. The modulation time estimation unit 24 arranges the read chromatogram data items according to the time lapse, thereby creating a one-dimensional chromatogram as shown in the diagram (a) of FIG. 3. Next, the entire curve of the created one-dimensional chromatogram is shifted in the positive direction (the right direction in the diagrams (a), (b) and (c) of FIG. 3) of the temporal axis by a predetermined shift time τ (refer to the diagram (b) of FIG. 3). While the shift time τ is gradually changed (the shift time is increased), the original (in a state of not being shifted at all) one-dimensional chromatogram is compared with the shifted one-dimensional chromatogram (hereinafter, called a "time-shifted one-dimensional chromatogram").

Since the resolution in the primary column 12 is relatively low, gas eluted from the primary column 12 contains the same compound spreading over multiple ranges of modulation time $t_m$. Accordingly, in the one-dimensional chromatogram, a peak originating from a certain one compound hardly appears only in one range of the modulation time $t_m$. In many cases, a sharp peak originating from the same compound appears in each of consecutive ranges of modulation time $t_m$. From the modulator 13 to the secondary column 14, compounds compressed at intervals of the modulation time $t_m$ are introduced. The same compound must have the same retention time in the secondary column 14. Accordingly, the interval between peaks that originate from the same compound and appear in respective adjacent ranges of modulation time $t_m$ on the one-dimensional chromatogram has regularity. The interval must coincide with the modulation time $t_m$. Accordingly, when the shift time $\tau$ coincides with the modulation time $t_m$, the positions of peaks originating from the same compound coincide with each other between the time-shifted one-dimensional chromatogram and the original one-dimensional chromatogram (refer to the diagram (c) FIG. 3). Thus, the modulation time estimation unit 24 obtains the shift time $\tau$ in the case where the peak positions coincide with each other as described above, thereby estimating the modulation time $t_m$.

More specifically, the regularity of peaks originating from the same compound on the one-dimensional chromatogram can be evaluated according to the following method.

Now, suppose the function of the curve of the one-dimensional chromatogram be f(t). An evaluation function with respect to the shift time $\tau$ as represented in Expression (1) is considered.

$$F(\tau)=\int f(t) \cdot f(t-\tau) dt \qquad (1)$$

This evaluation function is obtained by temporally integrating the product of the signal strengths at the same position (temporal position) between the original one-dimensional chromatogram and the time-shifted one-dimensional chromatogram.

The evaluation function of Expression (1) has peaks coinciding with each other and represents a significantly high value, when the shift time $\tau$ is an integral multiple of the modulation time $t_m$. Typically, the modulation time $t_m$ is set within a range of about one second to several tens of seconds, and thus the evaluation range of the shift time $\tau$ is preferably set to 0 seconds to about an extent ranging from at least 20 seconds to one minute. It is a matter of course that, if the setting range of the modulation time $t_m$ is narrower, the evaluation range of the shift time $\tau$ can also be set narrower. The integral calculation in Expression (1) may be replaced with total summation of the sampling intervals.

While the shift time $\tau$ is changed by each predetermined step width over the evaluation range of the shift time $\tau$ as described above, the evaluation value $F(\tau)$ based on Expression (1) is calculated. This calculation can obtain the relationship between the shift time $\tau$ and the evaluation value $F(\tau)$. As described above, if the shift time $\tau$ is twice, three times, . . . longer than the modulation time $t_m$, $F(\tau)$ becomes large. In the relationship between the shift time $\tau$ and the evaluation value $F(\tau)$, a predetermined number of shift times $\tau i$ at which $F(\tau)$ becomes a local maximum are selected in a descending order of $F(\tau)$. Here, $\tau 0$ (i=0)<$\tau 1$ . . . <$\tau n$. For example, n may be, say, about 1000. After the shift time $\tau i$ is thus obtained, it is preferred that $\Delta\tau 1=\tau 1-\tau 0$. If $m\Delta\tau 1$ resides in a range from $\tau 2$ to $\tau n$, $\Delta\tau 1$ is set as the modulation time $t_m$. If peaks originating from one compound eluted from the primary column 12 spread over consecutive four ranges of modulation time $t_m$ (typically, the resolution in the primary column 12 is set to such an extent), the value of m is set to all integers ranging from 2 to 4.

For determination whether $m\Delta\tau 1$ is in a range from $\tau 2$ to $\tau n$ or not as described above, in consideration of the peak width of the chromatogram and deviation in peak position due to variation in carrier gas flow velocity in the secondary column 14, it is preferred that an error to an extent of about, e.g., 20 ms be neglected.

If $m\Delta\tau 1$ does not reside in a range from $\tau 2$ to $\tau n$, setting is next made such that $\Delta\tau 2=\tau 2-\tau 0$ and it is determined whether $m\Delta\tau 2$ resides in a range from $\tau 3$ to $\tau n$ or not. If $m\Delta\tau 2$ resides in the range from $\tau 3$ to $\tau n$, $\Delta\tau 2$ is set as the modulation time $t_m$. If $m\Delta\tau 2$ does not reside in a range from $\tau 3$ to $\tau n$, it is preferred that $m\Delta\tau 1$ be obtained for higher $\tau i$ and a similar process be repeated. Thus, even if peaks capable of being regarded to originate from the same compound are not detected in adjacent ranges of modulation time owing to, e.g., disturbance, detection of peaks capable of being regarded to originate from the same compound in two or more ranges of modulation time that are not adjacent to each other (e.g., apart by one modulation time) enables a highly accurate modulation time to be estimated.

After the modulation time $t_m$ is thus estimated, the two-dimensional chromatogram creation unit 25 two-dimensionally arranges each chromatogram data item according to the obtained modulation time $t_m$, and creates the two-dimensional chromatogram as shown in FIG. 2C. Accordingly, even if the modulation time $t_m$ is not provided from the outside, i.e., operation input through the operation unit 5 or the reading of control data from the analysis control unit 3, the two-dimensional chromatogram based on the automatically estimated modulation time $t_m$ can be created.

The modulation time estimating method is not limited to the aforementioned method. Instead, the method may be any method as long as the method can detect the regularity or periodicity of appearance time of multiple peaks that can be estimated to originate from the same compound on the one-dimensional chromatogram. For example, the method is only required to evaluate correlation in waveform between the original one-dimensional chromatogram and the time-shifted one-dimensional chromatogram. Accordingly, any general method capable of calculating the correlation coefficient can be used.

It is apparent that the embodiment described above is merely an example of the present invention and it is obvious that any change, modification, or addition made as appropriate within the spirit and scope of the present invention is included in the scope of the appended claims. For example, the data processing apparatus according to the present invention is applicable not only to processing of data obtained by the comprehensive two-dimensional GC but also to processing of data obtained by the comprehensive two-dimensional LC.

REFERENCE SIGNS LIST

1 . . . Analysis Unit
11 . . . Sample Introduction Unit
12 . . . Primary Column
13 . . . Modulator
14 . . . Secondary Column
15 . . . Detector
2 . . . Data Processing Unit
21 . . . Data Collection Unit
22 . . . Data Storage Unit
23 . . . GC×GC Data Processor
24 . . . Modulation Time Estimation Unit
25 . . . Two-Dimensional Chromatogram Creation Unit
3 . . . Analysis control Unit
4 . . . Main control Unit
5 . . . Operation Unit
6 . . . Display Unit

The invention claimed is:

1. A comprehensive two-dimensional chromatograph, comprising:
a primary column configured to receive a sample gas;
a secondary column configured to receive compounds of the sample gas;

a modulator configured to transfer the compounds of the sample gas from the primary column to the secondary column;

a detector configured to detect the compounds in the comprehensive two-dimensional chromatograph and to output chromatogram data of the compounds;

a data processing apparatus configured to process the chromatogram data outputted by the detector, the data processing apparatus comprising:

a) a one-dimensional chromatogram creation unit configured to arrange chromatogram data items according to a chronological order of acquisition by the detector to create a one-dimensional chromatogram that represents a relationship between time and signal strength; and b) a modulation time estimation unit configured to estimate modulation time in the modulator, based on regularity in appearance time on the one-dimensional chromatogram between a certain peak and one or more other peaks that originate from a component identical to a component for the peak but appear at different time; and an output device configured to output a two-dimensional chromatogram having axes that are retention time in the primary column and retention time in the secondary column, based on the modulation time obtained by the modulation time estimation unit.

2. The comprehensive two-dimensional chromatograph according to claim 1, wherein the modulation time estimation unit is configured to examine correlation between the one-dimensional chromatogram and a time-shifted one-dimensional chromatogram obtained by shifting the one-dimensional chromatogram in a temporal axis, and estimate that a shift time maximizing the correlation during variation in the shift time is the modulation time.

3. The comprehensive two-dimensional chromatograph according to claim 2, further comprising a two-dimensional chromatogram creation unit configured to create the two-dimensional chromatogram.

4. The comprehensive two-dimensional chromatograph according to claim 1, further comprising a two-dimensional chromatogram creation unit configured to create the two-dimensional chromatogram.

* * * * *